United States Patent

Kawakami et al.

Patent Number: 5,405,508
Date of Patent: Apr. 11, 1995

[54] METHOD FOR REGENERATING TETRAALKYLAMMONIUM HYDROXIDE

[75] Inventors: Chisako Kawakami, Kurashiki; Hitoshi Satoh, Okayama, both of Japan

[73] Assignee: Chlorine Engineers Corp. Ltd., Tokyo, Japan

[21] Appl. No.: 282,903

[22] Filed: Jul. 29, 1994

[30] Foreign Application Priority Data

Jul. 29, 1993 [JP] Japan ................. 5-188507

[51] Int. Cl.$^6$ ............................. B01D 61/44
[52] U.S. Cl. ..................... 204/102; 204/131; 204/182.4
[58] Field of Search .......... 204/102, 131, 182.4

[56] References Cited

U.S. PATENT DOCUMENTS 4,714,530 12/1987 Hale et al. ................. 204/131

Primary Examiner—John Niebling
Assistant Examiner—Arun S. Phasge
Attorney, Agent, or Firm—Kuhn and Muller

[57] ABSTRACT

The present invention relates to a method for regenerating tetraalkylammonium hydroxide used as developer solution for positive type resist from waste developer solution. Waste solution from developer solution for positive type resist, which contains tetraalkylammonium hydroxide as principal component, is neutralized, and after depositing and removing alkali-soluble organic substances dissolved in it, it is electrolyzed in an anode chamber of an electrolytic cell partitioned by cation exchange membranes, and it is anodized in the anode chamber. Aqueous solution of tetraalkylammonium hydroxide obtained from the cathode chamber is further introduced to an anode chamber of the other electrolytic cell to perform multi-stage electrolysis or it is introduced into an anode chamber of an electrolytic cell partitioned into 3 chambers or more by two or more cation exchange membranes to perform multi-chamber electrolysis. The electrolytic solution of the intermediate chamber is circulated to an electrolytic cell for decomposing organic substances and electrolyzed, and tetraalkylammonium hydroxide, which can be re-used as developer solution, is obtained from the cathode chamber of the final stage electrolytic cell or from the cathode chamber of the multi-chamber electrolytic cell.

6 Claims, 3 Drawing Sheets

METHOD FOR REGENERATING TETRAALKYLAMMONIUM HYDROXIDE

BACKGROUND OF THE INVENTION

The present invention relates to a method for regenerating tetraalkylammonium hydroxide to be used as a developer in fine fabrication of circuit pattern and the like by photolithography in the manufacturing processes of integrated circuits such as LSIs or ultra LSIs or liquid crystal display units.

Semiconductor integrated circuits such as ICs, LSIs, ultra LSIs, etc. are produced as follows: Photo resist is coated on a substrate such as silicon wafer, and a desired pattern is put on it by exposure using a stepper. Then, photolithography process such as developing, etching, etc. are repeated. Thin film transistor (TFT) for liquid crystal display unit is also manufactured by photolithography process on a glass substrate.

Photo resist is divided into a negative type resist, in which irradiated portion is insolubilized by exposure of circuit pattern, and a positive type resist, in which irradiated portion is solubilized.

As a typical positive type photo resist, novolak resin containing photosensitive substance such as o-diazonaphthoquinone is used. An example of a mixture of esterized o-diazonaphthoquinone sulfonic acid ester and m-cresol type novolak resin is given by the following chemical formula:

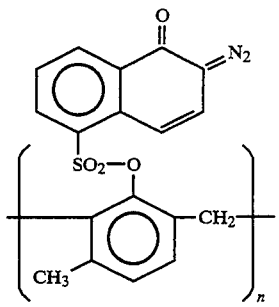

The o-diazonaphthoquinone sulfonyl group combined with novolak resin gives an effect to decrease solubility of novolak resin. When light such as ultraviolet ray is irradiated on o-diazonaphthoquinone, it is turned to ketene, and 3-indene-carboxylic acid is further genenerated under the presence of water:

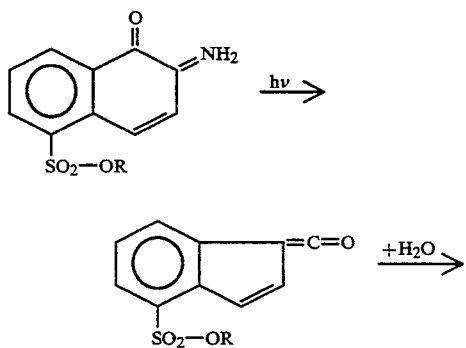

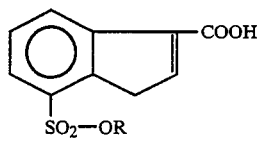

As the result, o-diazonaphthoquinone not only ceases to give effect as a dissolution inhibitor for novolak resin, but the alkali solubility is increased because acid is generated. Therefore, when a positive type photo resist with an exposed circuit pattern is developed by alkali solution, the exposed portion is dissolved by alkali solution, and a positive image is formed.

As alkali developer for the positive type resist, alkali carbonate, aqueous ammonia, tetramethylammonium hydroxide, etc. are used. With the increase of the devices with higher integration such as LSI, there are strong demands on the decrease of impurities in chemical agents to be used in the manufacturing process. Above all, there is strict restriction on intermingling of metal ions in the semiconductor manufacturing process. As the result, the developers containing tetramethylammonium hydroxide, which is an alkali solution containing no metal ion as main component, is now widely used in the process of photolithography.

Aqueous solution of hydroxide of tetraalkylammonium such as tetramethylammonium hydroxide used as a developer for the positive type photo resist had been disposed in the past as waste solution. This waste solution contains organic substances such as novolak resin, which is a major component of photo resist, and hydroxide of tetraalkylammonium contains nitrogen, which is turned to eutrophic component in water and causes contamination and deterioration of water quality. Thus, this has been disposed through various treatment procedures. With the increase in the quantity of developer used for the manufacture, the quantity of waste solution to be disposed also increased, and there have been urgent demands on the utilization of waste solution and on the decrease of the waste solution.

The present inventors have proposed a method for obtaining high purity tetraalkylammonium hydroxide from a cathode chamber in the Japanese Patent Application No. 2-408052 by introducing the waste solution into an anode chamber of an electrolytic cell, which is divided by a perfluorinated cation exchange membrane. According to this method, organic substances of novolak resin type in the waste solution, which is introduced into an anode chamber of an electrolytic cell, do not adversely affect the cation exchange membrane or move into the cathode chamber. But, when electrolysis is continued, concentration of organic substances such as novolak resin in the anode chamber increases, and the anode solution with increased organic substance concentration must be disposed, and it is impossible to completely regenerate and utilize tetraalkylammonium hydroxide in the waste solution.

Further, as a method for suppressing the increase of concentration of organic substances such as alkali-soluble novolak resin, which is accumulated in anode chamber when electrolysis is continuously performed, the present inventors have proposed a method in Japanese Patent Laid-Open Publication 5-7889 (U.S. patent application Ser. No. 08/68277 U.S. Pat. No. 5,354,434), in which carbon dioxide is introduced to neutralize waste developer solution and, after alkali-soluble organic substances are dissolved in it, electrolysis is performed in an anode chamber of electrolytic cell partitioned by a perfluorinated cation exchange membrane to obtain high purity tetraalkylammonium hydroxide from cathode chamber.

According to this method, waste developer solution is sent from the waste solution tank 1 to a neutralizing process 2 as shown in FIG. 3, and after carbon dioxide is blown in for pH adjustment, precipitated alkali-soluble substances are removed in a filtration process 3. Then, water component is separated in a condensation process 4, and organic solvents or surface active agents are reduced in an organic substance removal process 5, and it is sent to an anode chamber 8 of the electrolytic cell 6 partitioned by cation exchange membrane 7. Then, aqueous solution of tetraalkylammonium hydroxide is collected from the cathode chamber 9, and carbon dioxide generated in the anode chamber is re-used in the neutralization process.

In this method, however, water-soluble low grade organic substances of ethyl cellosolve type to be used as solvent for photo resist remain in the waste developer solution after neutralization and microfiltration as they are introduced into the anode chamber of the electrolytic cell. As the result, low grade substances increase in the anode solution as electrolysis is continued, and a part of them are dialyzed through the cation exchange membrane during electrolysis and is contained in tetraalkylammonium hydroxide collected in the cathode chamber. COD (Mn) value reaches as high as about 1000 ppm, and this is far higher than the level of less than 10 ppm in high purity tetraalkylammonium hydroxide commercially available as developer, and this is not desirable in some applications.

Under such circumstances, it has been proposed to design the electrolytic cell in multiple stages, or the solution is collected from the cathode chamber through at least two cation exchange membranes using a multi-chamber electrolytic cell. By this method, however, low grade organic substances migrate toward the cathode chamber as electrolysis is continued. To raise removal ratio of the low grade organic substances, a method has been proposed in Japanese Patent Laid-Open Publication 5-106074 (U.S. patent application Ser. No. 08/168277), in which ozone prepared by an ozone generator is supplied to aqueous solution of tetraalkylammonium hydroxide containing low grade organic substances, which passed through the first cation exchange membrane, in order to oxidize and decompose and to reduce content of low grade organic substances, and high purity tetraalkylammonium hydroxide with lower content of low grade organic substances can be obtained. Although removal ratio of organic substances contained as impurities is high, it is necessary to provide an ozone generator, an additional means for promoting reaction with ozone, an apparatus for decomposing unreacted ozone, etc. Also, alkylamine odor often occurs in tetraalkylammonium hydroxide obtained from the cathode chamber when the solution in an intermediate chamber of the multi-chamber electrolytic cell is continuously oxidized by high concentration ozone for long period. This may be attributable to the fact that tetraalkylammonium hydroxide is slightly decomposed and alkylamine is generated. The presence of alkylamine can be identified by odor even when it is present in such small quantity that it cannot be detected by an analyzer and it gives no effect on tetraalkylammonium hydroxide. Thus, there have been strong demands on tetraalkylammonium hydroxide which does not generate alkylamine.

It is an object of the present invention to provide a method for regenerating tetraalkylammonium hydroxide, which contains very low content of low grade organic substances as impurities, whereby there is no need to provide an ozone generator, an apparatus for promoting reaction with the solution to be treated, an apparatus for decomposing unreacted ozone, etc. as required in oxidation and decomposition of low grade organic substances by ozone, and oxidation and decomposition can be adjusted in easy and simple manner.

SUMMARY OF THE INVENTION

To attain the above object, the method for regenerating tetraalkylammonium hydroxide according to the present invention is characterized in that aqueous solution of a used tetraalkylammonium compound containing organic substances as impurities is neutralized, and after separating and removing insoluble components, the solution is sent to an anode chamber of an electrolytic cell partitioned by cation exchange membrane, and tetraalkylammonium hydroxide is obtained from a cathode chamber, whereby a cathode solution obtained from a first stage electrolytic cell is supplied to an anode chamber of a next stage electrolytic cell to electrolyze, and tetraalkylammonium hydroxide is obtained, and organic substances contained as impurities at least in an anode chamber of either one of the electrolytic cells are anodized.

Also, the method for regenerating tetraalkylammonium hydroxide of the present invention is characterized in that aqueous solution of a used tetraalkylammonium compound containing organic substances as impurities is neutralized, and after separating and removing insoluble components, the solution is sent to an anode chamber of an electrolytic cell partitioned by cation exchange membrane, and tetraalkylammonium hydroxide is obtained from a cathode chamber, whereby the solution is supplied to an anode chamber of a multi-chamber electroyltic cell partitioned by a plurality of cation exchange membranes to electrolyze, and organic substances contained as impurities are anodized and tetraalkylammonium hydroxide is obtained from the cathode chamber.

Also, the present invention provides a method for regenerating tetraalkylammonium hydroxide, in which, after a cathode solution prepared in a first stage electrolytic cell has been neutralized, it is supplied to an anode chamber of a next stage electrolytic cell and tetraalkylammonium hydroxide is obtained from a cathode chamber of a final stage electrolytic cell.

Further, the invention provides a method for regenerating tetraalkylammonium hydroxide, in which electrolytic solution in an intermediate chamber of a multi-chamber electrolytic cell partitioned by cation exchange membranes is circulated in an anode chamber of an electrolytic cell for decomposing organic substances, and organic substances contained in the electrolytic solution are anodized to reduce concentration of organic substances.

DESCRIPTION OF THE PREFERRED EMBODIMENTS

Figure 1:
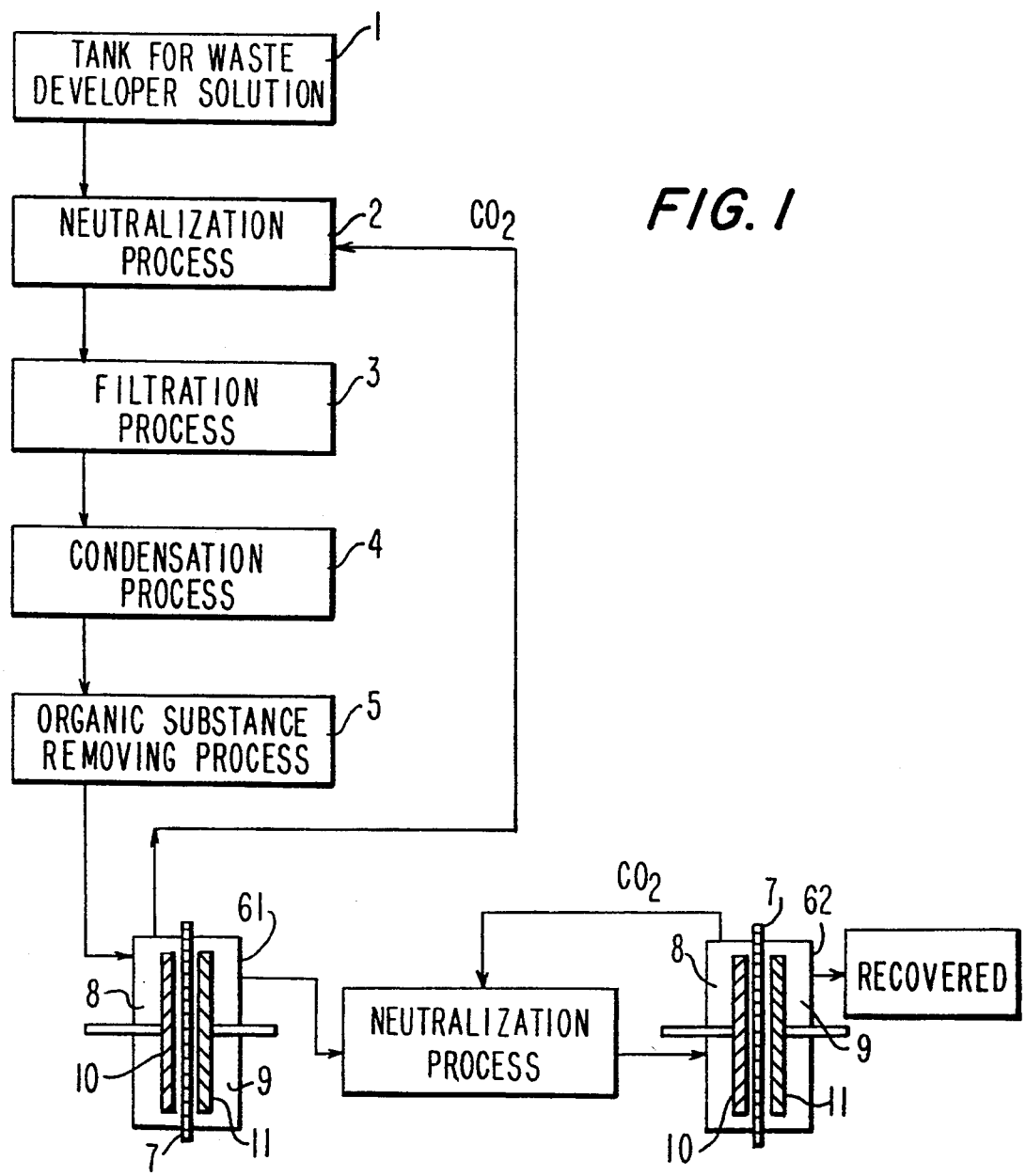
FIG. 1 is a chart for explaining a method for regeneration by a multi-stage electrolysis method of the present invention.

Specifically, the method according to the present invention is to obtain aqueous solution of high purity tetraalkylammonium hydroxide for re-utilization of developer solution which contains tetraalkylammonium hydroxide used as positive type resist developer solution in the manufacturing process of semiconductor devices. Various types of materials used in fine fabrication in the manufacture of semiconductor devices such as LSI are in very high purity. In the process to use developer solution, the quantity of intermingled impurities such as metallic ions is extremely low, and the impurities in waste solution, in which principal component is aqueous solution of tetramethylammonium hydroxide used as developer solution for positive type resist, include macromolecular organic substances of novolak resin type, which is the component of positive type photo resist, surface active agents, ethyl cellosolve type organic solvents, etc., and the intermingling of metallic components such as alkali metal ions, which is regarded as an important issue in the manufacturing process of semiconductor device, is negligible. The low grade organic substances of ethyl cellosolve type used as solvent for photo resist are mostly evaporated in photo resist baking process, and the quantity of low grade organic substances intermingled into the developer solution is relatively small, and most of unnecessary organic substances contained in the waste solution are macromolecular organic substances such as novolak resin.

Since the photo resist such as novolak resin has carboxylic acid group and is dissolved in alkaline developer containing tetraalkylammonium hydroxide, when it is neutralized by adding acid, novolak resin is deposited as insoluble organic substance, and this can be separated by method such as filtration from the solution. This makes it possible to reduce the content of unnecessary organic substance in the waste solution to very low value.

For neutralization of the waste solution, it is possible to use various types of acids to neutralize alkali or various substances to generate acid when dissolved, but it is not desirable to use those substances such as anions including chlorine ion, sulfate ion, nitrate ion or the substances containing metal compounds which adversely affect when tetramethylammonium hydroxide is re-utilized in photolithography process. It is also not desirable to use organic acids, which adversely affect electrodes of the electrolytic cell or ion exchange membrane. Therefore, it is preferable to use carbonic acid or carbon dioxide, which does not generate undesirable anions. Further, carbonic acid increases the quantity of water in the waste solution, and it is more preferable to introduce gaseous carbon dioxide, which does not increase liquid quantity in the waste solution, into the waste solution for reaction.

When carbon dioxide is introduced into the waste solution, the following reaction occurs with tetraalkylammonium hydroxide, and bicarbonate or carbonate of tetraalkylammonium are generated, and the carbonate is further turned to bicarbonate.

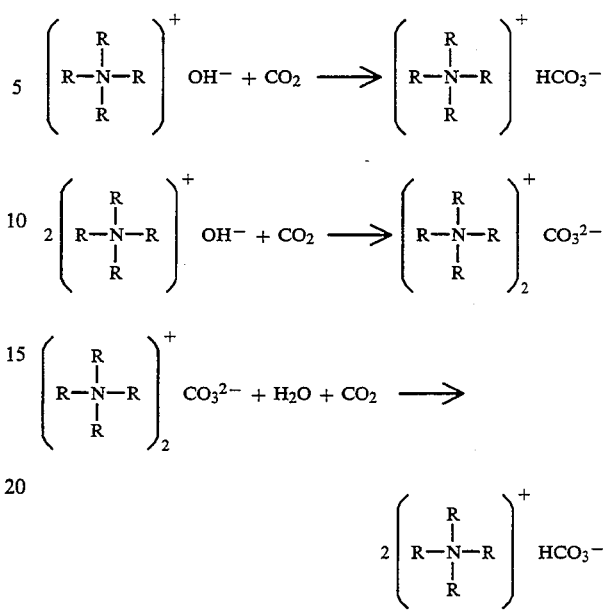

where

R represents and alkyl group.

As the result of neutralization, novolak resin dissolved in alkali is not any more dissolved in water and is deposited. After separating the deposited novolak resin through filtration membrane, the waste solution is introduced into the anode chamber of the electrolytic cell partitioned by a perfluorinated cation exchange membrane and electrolyzed, and the following chemical reaction occurs.

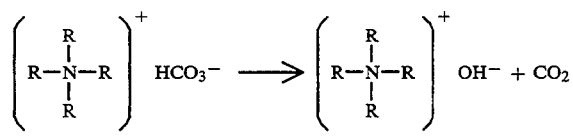

where

R represents an alkyl group.

In the anode chamber, carbon dioxide, oxygen, etc. are generated, and tetraalkylammonium ions move into the cathode chamber from the anode chamber through the cation exchange membrane, generating high purity tetraalkylammonium hydroxide.

Description will be given below on the method for regenerating tetraalkylammonium hydroxide of the present invention, referring to the drawings.

FIG. 1 is a chart for explaining a method of regeneration by two-stage electrolysis.

On the other hand, the developer waste solution is sent from a waste solution tank 1 to a neutralization process 2 as shown in FIG. 1, where carbon dioxide gas is blown in, and pH value is adjusted. It is desirable to bring pH value as close to neutrality as possible in view of corrosion-resistant property of the filtration membrane in a filtration process 3. It is preferable to adjust pH value to 10 or lower, or more preferably, to about 8.

After removing organic substances in the filtration process, the waste solution is sent to a condensation process 4, where water is separated and the solution is condensed. Electrolysis can be performed without passing through the condensation process, but it is generally not very efficient to directly perform electrolysis because concentration of tetraalkylammonium compounds in the developer waste solution is as low as several weight %. Thus, it is preferable to increase electrolysis efficiency by condensing the solution to 5–60 weight %, or more preferably, to 15–40 weight %.

The neutralization process must be performed before the filtration process, while the condensation process may be performed after the filtration process or before the neutralization process.

The waste solution condensed in the condensation process is sent to an organic substance removing process 5 where soluble organic substances are decomposed. In case organic substances of ethylcellosolve type or surface active agent used as solvents for novolak resin are contained in large quantity, ion exchange membrane may be adversely affected, or bubbling may occur in the electrolytic cell by bubbles generated during electrolysis, or organic substances may be contained in tetraalkylammonium hydroxide obtained from the cathode chamber through cation exchange membrane. Thus, it is necessary to decrease the content of organic substances by decomposing them.

To decompose organic substances, there are methods to decompose by hydrogen peroxide, by ultraviolet ray or oxidizing decomposition by ozone. In particular, it is preferable to anodize it in an anode chamber of an electrolytic cell, The method by anodizing can also be achievable by simply replacing with an electrode with higher oxygen overvoltage as anode. Thus, it is possible to effectively oxidize and decompose without requiring many additional equipment and devices.

The waste solution processed in the organic substance removal process is sent to an anode chamber of a first stage electrolytic cell 61 in the multi-stage electrolysis process where 2-chamber type electrolytic cells are arranged in multiple stages.

The electrolytic cell is partitioned to an anode chamber 8 and a cathode chamber 9 by perfluorinated cation exchange membranes 7. As the perfluorinated cation exchange membrane, sulfonic acid type ion exchange membrane such as Nafion 324 (mnaufactured by Dupont) may be used. As the anode 10, an electrode with a metal of platinum family or its oxide coated on corrosion-resistant base material or an electrode having highly corrosion-resistant property in oxidizing atmosphere such as magnetite may be used. In particular, it is preferable to use an electrode with high oxygen overvoltage and anodizing power such as lead dioxide electrode with $\beta$-$PbO_2$ coated on it. Some of the electrodes with high oxygen overvoltage contain such substance as platinum, which is likely to form complex with organic substances and this may consume coating of the electrode in earlier stage. Therefore, it is essential to adequately select it based on the organic components contained therein. As the cathode 11, a metal resistant to alkali such as stainless steel, nickel, etc. may be used. Because carbon dioxide and oxygen are generated at the anode and gases such as hydrogen are generated at the cathode due to electrolytic reaction, it is preferable to use expanded metal, screen, perforated plate, etc. as base material for anode or cathode.

The electrode with high oxygen overvoltage can provide good effects when it is used as the anode in all electrolytic cells or it is used at least in one electrolytic cell in the first stage or the next stage. By the use of such electrodes as anodes in all electrolytic cells, it is possible to increase the effect to remove low grade organic substances in the products. When the tetraalkylammonium hydroxide obtained in the cathode chamber of the first stage electrolytic cell in the multi-stage electrolysis process is supplied to the anode chamber of the next stage electrolytic cell 62 without changing its strong alkalinity, the potential to generate oxygen is decreased, and the lead dioxide electrode or the ion exchange membrane are often damaged. Thus, it is preferable to neutralize it with carbon dioxide before sending it to adjust pH value to neutral level and to increase oxidizing power of organic substances by raising the potential to generate oxygen.

By the above method, it is possible to obtain aqueous solution of tetraalkylammonium hydroxide with lower content of low grade organic substances from the cathode chamber of the final stage electrolytic cell.

Incidentally, anodizing as mentioned in the present invention means electrochemical decomposition of low grade organic substances in anode chamber as well as catalytic decomposition by lead dioxide in addition to oxidizing reaction in the anode chamber of the electrolytic cell.

Figure 2:
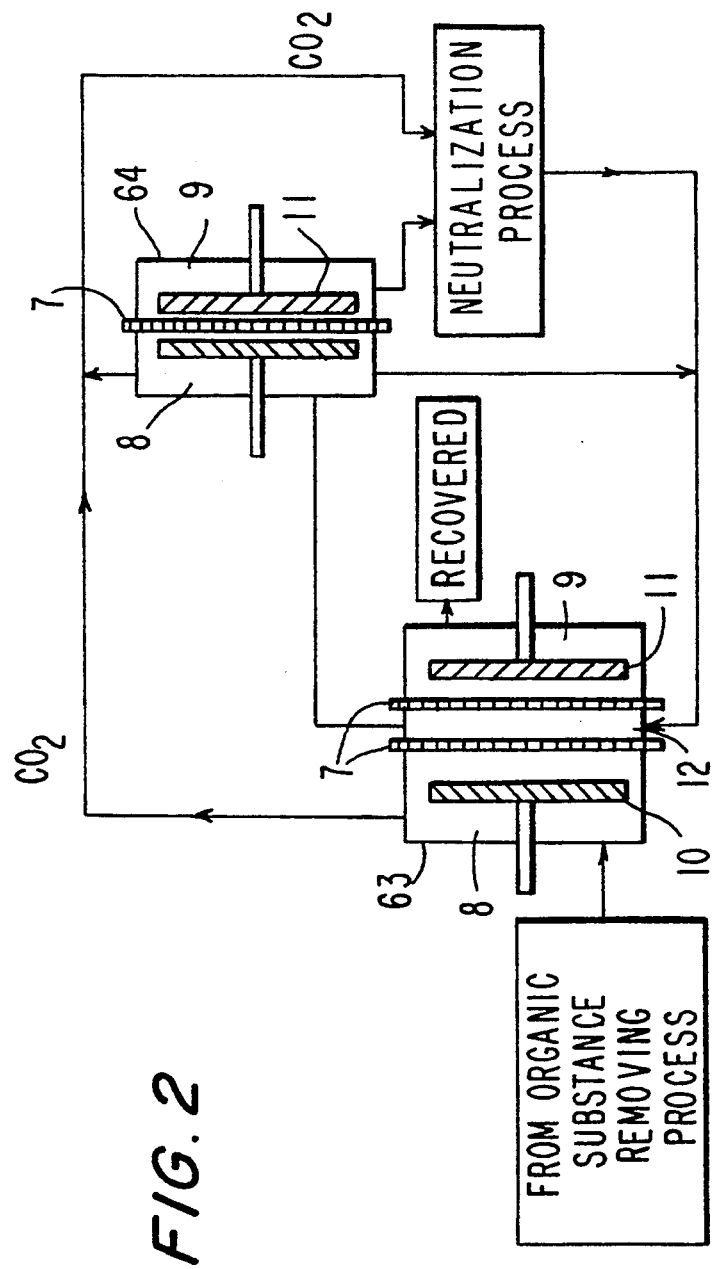
FIG. 2 is a schematical drawing for explaining a method for regeneration according to multi-chamber electrolysis method of the present invention.
Figure 3:
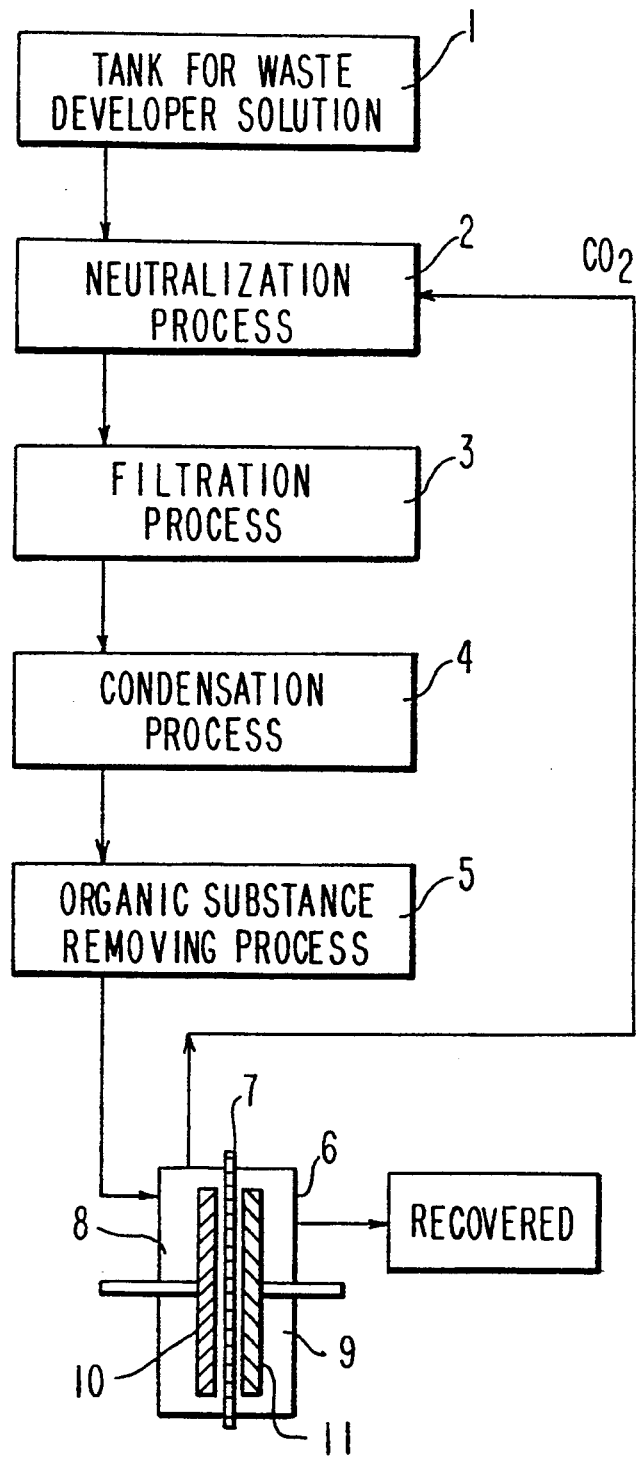
FIG. 3 is a chart for explaining a method for regenerating tetraalkylammonium hydroxide by electrolysis.

FIG. 2 is a schematical drawing for explaining a method of multi-chamber electrolytic cell in the electrolysis process.

In the multi-chamber electrolysis process, the solution is neutralized and filtered similarly to the process in multi-stage electrolysis, and it is sent to an anode chamber of a 3-chamber electrolysis cell 63 partitioned by two cation exchange membranes. To remove low grade organic substances, which passed through the cation exchange membranes, electrolytic solution in an intermediate chamber 12 is sent to an anode chamber in an electrolytic cell 64 for decomposing organic substances with the anode having high oxgygen overvoltage. Thus, the solution is circulated while organic substances are anodized. By providing the anode chamber of 3-chamber electrolytic cell with an anode having high oxygen overvoltage, organic substances can be effectively oxidized and decomposed, and aqueous solution of tetraalkylammonium hydroxide with lower content of low grade organic substances can be obtained from the cathode chamber of 3-chamber electrolytic cell.

In case aqueous solution of tetraalkylammonium hydrogencarbonate in the intermediate chamber is circulated to the anode chamber of the electrolytic cell for decomposing organic substances and is anodized, tetramethylammonium ions pass through ion exchange membranes in the 2-chamber electrolytic cell and are moved to the cathode chamber, and it is necessary to supply tetraalkylammonium hydrogencarbonate to the circulating solution. By neutralizing tetraalkylammonium hydroxide generated in the cathode chamber of the electrolytic cell for decomposing organic substances with carbon dioxide and by supplying and circulating the tetraalkylammonium hydrogencarbonate in the circulating solution, concentration of impurities in the circulating solution can be reduced, and it is possible to maintain pH value in the intermediate chamber with a predetermined range, to keep the potential for anodizing at high level and to retain anodizing power.

For the multi-stage electrolysis process, a 2-stage example has been given, and 3-chamber electrolytic cell has been shown as multi-chamber electrolytic cell. However, multi-stage electrolysis process using 3 stages or more may be used in 2-chamber type electrolytic cell, and multi-chamber electrolytic cell having 3 chambers or more may be used as multi-chamber electrolytic cell. The intermediate chamber in the present invention means a partitioned chamber in an electrolytic cell where anode or cathode is not present. Mixed gas of carbon dioxide and oxygen generated in the anode chamber of these electrolytic cells may be used to neutralize alkalinity in the neutralization process.

In the electrolysis method of the present invention, current density of electrolysis may be 2 to 50 A/dm$^2$, and it is preferable that current density is 2 to 30 A/dm$^2$ to keep adequate service life of the electrode and ion exchange membrane.

The method for regenerating of the present invention may be performed at a site where developer solution is used or at a facility with centralized processing installation.

In the following, detailed description will be given on embodiments of the present invention:

(Example 1)

(Process to prepare neutralized developer waste solution)

To bottom surface of a 10-liter container lined with fluororesin on its inner surface, 50 g of novolak type positive photo resist (OFPR-800; Tokyo Ohka Industry Co., Ltd.) was lightly coated, and this was pre-baked in a hot air dryer at 90° C. for 120 minutes. Ethylcellosolve acetate and other volatile organic solvents in the resist were removed by evaporation, and after exposing to irradiation of ultraviolet ray for 60 seconds using a low voltage mercury lamp (450 W; Oak Manufacturing Co., Ltd.), 6 liters of high purity 5 weight % tetramethylammonium hydroxide aqueous solution were added to a stainless steel container, and photo resist was developed and dissolved.

Next, blowing high purity nitrogen into this developer waste solution, moisture was evaporated in a hot air dryer at 90° C., and the solution was condensed to ⅓. After condensation, tetramethylammonium hydroxide in the developer waste solution was 4.8 weight % in concentration, 7,000 ppm in COD (Mn) value, and 14.0 in pH value.

Into the developer waste solution after condensation, high purity carbon dioxide was blown at a rate of 1.5 liters/min. for neutralization. Blowing of the carbon dioxide caused bubbling in the developer waste solution. When it was neutralized from pH 14 to pH 8, precipitates of novolak resin was generated in the waste solution.

Then, the developer waste solution after neutralization was filtered by precision filtration using an ultrafiltration membrane with molecular weight of 15,000. Thus, insoluble organic substances were filtered and separated to obtain neutralized waste solution. Tetramethylammonium hydrogencarbonate in the neutralized developer waste solution was 15 weight % in concentration, 3,300 ppm in COD (Mn) value, and 8.0 in pH value.

(Electrolysis process)

For the 3-chamber electrolytic cell, a filter press type electrolytic cell having a pair of anode and cathode with an effective electrode area of 0.2 dm$^2$ was used. Using two pieces of Nafion 324 (manufactured by Dupont), i.e. perfluorinated cation exchange membranes, the electrolytic cell was partitioned to an anode chamber, an intermediate chamber and a cathode chamber. In the anode chamber of the electrolytic cell, an anode of titanium electrode coated with lead dioxide (Permelec Electrode Co., Ltd.) was arranged, and a cathode comprising nickel was disposed in the cathode chamber. The solution was circulated between the anode chamber and a polyethylene container filled with neutralized waste developer solution at flow rate of 5 liters/hour. In the intermediate chamber, aqueous solution of high purity tetramethylammonium hydrogencarbonate of 5.0 weight % concentration was filled in a polyethylene container of 1.0 liter volume, and the solution was sent from the polyethylene container at flow rate of 5 liters/hour by pump. Overflow solution from the intermediate chamber was circulated to the polyethylene container. In the cathode chamber, aqueous solution of high purity tetramethylammonium hydroxide of 15.0 weight % concentration was filled in a polyethylene container of 1.0 liter volume, and it was supplied from the polyethylene container at flow rate of 5 liters/hour by pump. Overflow solution was circulated to the polyethylene container, and ultra pure water was added to the cathode solution, and concentration of the cathode solution was maintained at a constant level. Then, electrolysis was performed at electrolysis temperature of 50° C., constant current density of 10 A/dm$^2$ and electrolysis voltage within the range of 8 to 10 V.

In the anode chamber of 3-chamber type electrolytic cell, the solution with COD (Mn) of 3,300 ppm as organic substance content was contained when electrolysis was started. At 48 hours after starting of electrolysis, it was 3,500 ppm. The measured value of COD (Mn) of aqueous solution of high purity tetramethylammonium hydrogen-carbonate of 5.0 weight % concentration filled as the intermediate chamber solution was less than 10 ppm when the electrolysis was started, and 900 ppm at 48 hours after the starting of electrolysis. The measured value of COD (Mn) of aqueous solution of high purity tetramethylammonium hydroxide of 15.0 weight % concentration filled in the cathode chamber was less than 10 ppm at the starting of electrolysis and 20 ppm at 48 hours after starting of electrolysis.

(Example 2)

An intermediate chamber solution of 3-chamber electrolytic cell having the same arrangement as in Example 1 was circulated between 3-chamber electrolytic cell and an electrolytic cell for decomposing organic substances using cation exchange membranes and electrode at flow rate of 5 liters/hours. To the cathode chamber of 2-chamber type electrolytic cell, aqueous solution of tetramethylammonium of 5 weight % concentration was supplied from a polyethylene container at flow rate of 5 liters/hour, and the solution was circulated between the cathode chamber and the polyethylene container.

In the 3-chamber electrolytic cell, electrolysis was performed at electrolysis temperature of 50° C., constant current density of 10 A/dm$^2$, and electrolysis voltage of 17 to 12 V. In the 2-chamber electrolytic cell, electrolysis was performed at electrolysis temperature of 30° C., constant current density of 2 A/dm$^2$ and electrolysis voltage of 7.5 to 8.8 V.

The measured value of COD (Mn) of the anode solution supplied to the 3-chamber electrolytic cell was 3,250 ppm at the starting of electrolysis, and it was 3,260 ppm at 48 hours after the starting of electrolysis. The measured value of COD (Mn) in the intermediate chamber was less than 10 ppm at the starting of electrolysis, and it was 1,100 ppm at 48 hours after the starting of electrolysis. The measured value of COD (Mn) of the cathode solution was 10 ppm at the starting of electrolysis, and it was less than 10 ppm at 48 hours after the starting of electrolysis.

The concentration impurities in aqueous solution of tetramethylammonium hydroxide of 16.7 weight % concentration elecrolyzed and collected as the cathode solution from the cathode chamber of each of 3-chamber and 2-chamber electrolytic cells was less than 10 ppb in all of Na, K, Fe, Cr, Ni, Mg, Ca, Cu and Pb.

On the other hand, at 24 hours after the starting of electrolysis, concentration of tetramethylammonium hydroxide decreased to 5 weight %, and concentration of tetramethylammonium hydroxide in the cathode solution increased to 16.7 weight %.

The concentration of impurities in aqueous solution of tetramethylammonium hydroxide of 16.7 weight % concentration electrolyzed and collected as cathode solution was less than 10 ppb in all of Na, K, Fe, Cr, Ni, Mg, Ca, Cu and Pb.

(Comparative example 1)

Aqueous solution of tetramethylammonium hydroxide was regenerated by the same procedure as in Example 1, except that the lead dioxide electrode at the anode was replaced with an electrode coated with iridium oxide (manufactured by Permelec Electrode Co., Ltd.).

At the starting of electrolysis, the measured value of COD (Mn) of anode solution in 3-chamber electrolytic cell was 3,300 ppm, while it was 5,300 ppm at 48 hours after the starting of electrolysis. The measured value of COD (Mn) of aqueous solution of high purity tetramethylammonium hydrogencarbonate of 5.0 weight % concentration filled as the intermediate chamber solution was less than 10 ppm at the starting of electrolysis, while it was 1,500 ppm at 48 hours after the starting of electrolysis. The measured value of COD (Mn) of aqueous solution of high purity tetramethylammonium hydroxide of 15.0 weight % concentration filled as anode solution was less than 10 ppm at the starting of electrolysis and 700 ppm at 48 hours after the starting of electrolysis.

(Comparative example 2)

Aqueous solution of tetramethylammonium hydroxide was regenerated by the same procedure as in Example 2, except that the lead dioxide electrode of anode was replaced with an electrode coated with iridium oxide (manufactured by Permelec Electrode Co. Ltd.).

At the starting of electrolysis, the measured value of COD (Mn) of the anode solution in 3-chamber electrolytic cell was 3,300 ppm, while it was 5,300 ppm at 48 hours after the starting of electrolysis. The measured value of COD (Mn) of aqueous solution of high purity tetramethylammonium hydrogencarbonate of 5.0 weight % concentration was less than 10 ppm at the starting of electrolysis, while it was 1,500 ppm at 48 hours after the starting of electrolysis. The measured value of COD (Mn) of aqueous solution of high purity tetramethylammonium hydroxide of 15.0 weight % concentration was less than 10 ppm at the starting of electrolysis and 700 ppm at 48 hours after the starting of electrolysis.

As described above, tetraalkylammonium hydroxide, which has been disposed in the past as waste solution after it was used as developer solution for positive type photo resist in photolithography in the manufacturing process of semiconductor devices, was neutralized using carbon dioxide. As a result, organic substances dissolved in alkali were deposited, and precipitates of insoluble organic substances in waste solution can be removed by filtration membrane. After the removal of organic substances by filtration, the waste solution was introduced into anode chamber of electrolytic cell partitioned by cation exchange membranes and was electrolyzed. After neutralizing aqueous solution of tetraalkylammonium hydroxide from the cathode chamber, it was introduced into anode chamber of the other electrolytic cell and was anodized. Then, multi-stage electrolysis was performed to introduce the solution to anode chamber of the other electrolytic cell and anodize and to collect tetraalklylammonium hydroxide from cathode chamber, or multi-chamber electrolysis was performed to introduce the solution into anode chamber of electrolytic cell partitioned into 3 chambers or more by two or more cation exchange membranes to circulate the electrolytic solution of the intermediate chamber to anode chamber of the electrolytic cell for anodizing, and electrolysis was performed while anodizing low grade organic substances. As a result, compared with the method to oxidize and decompose low grade organic substances by ozone, there is no need to provide additional equipment and devices such as ozone generator or an apparatus for decomposing unreacted ozone. Content of low grade organic substances from the cathode chamber is low, and it is possible to obtain high purity tetraalkylammonium hydroxide, which can be re-used as developer solution.

What we claim are:

1. A method for regenerating tetraalkylammonium hydroxide, comprising the steps of:
    neutralizing an aqueous solution containing a used tetraalkylammonium compound having organic substances as impurities,
    separating and removing insoluble components before feeding the solution to an anode chamber of a first stage electrolytic cell partitioned by a cation exchange membrane into anode and cathode chambers, to obtain tetraalkylammonium hydroxide from said cathode chamber,
    supplying a cathode solution obtained from said first stage electrolytic cell to an anode chamber of a next stage electrolytic cell to electrolyze said solution,
    wherein tetraalkylammonium hydroxide is obtained in said cathode chamber, and organic substances contained as impurities at least in an anode chamber of either stage of the electrolytic cells are anodized.

2. A method for regenerating tetraalkylammonium hydroxide according to claim 1, further comprising neutralizing the cathode solution obtained in the first stage electrolytic cell, before it is supplied to the anode chamber of the next stage electrolytic cell to electrolyze said solution, and tetraalkylammonium hydroxide is obtained from a cathode chamber of the next stage electrolytic cell.

3. A method for regenerating tetraalkylammonium hydroxide according to claim 1, wherein said anodizing is performed by an anode, which has an electrode catalytic substance containing lead dioxide.

4. A method for regenerating tetraalkylammonium hydroxide, comprising the steps of neutralizing an aqueous solution containing a used tetraalkylammonium compound having organic substances as impurities,
    separating and removing insoluble components before feeding the solution to an anode chamber of a first stage electrolytic cell partitioned by a cation exchange membrane into anode and cathode chambers, to obtain a tetraalkylammonium hydroxide solution from said cathode chamber, supplying the solution to an anode chamber of a multi-chamber electrolytic cell partitioned by a plurality of cation exchange membranes, wherein organic substances contained as impurities are anodized, and tetraalkylammonium hydroxide is obtained from the cathode chamber.

5. A method for regenerating tetraalkylammonium hydroxide according to claim 4, further comprising an electrolytic solution from an intermediate chamber of said multi-chamber electrolytic cell partitioned by cation exchange membranes is circulated to an anode chamber of an electrolytic cell for decomposing organic substances, wherein organic substances contained in the electrolytic solution as impurities are anodized, and concentration of organic substances is decreased.

6. A method for regenerating tetraalkylammonium hydroxide according to claim 4, wherein said anodizing is performed by an anode, which has an electrode catalytic substance containing lead dioxide.

* * * * *